(12) United States Patent
Stanton

(10) Patent No.: US 10,682,129 B2
(45) Date of Patent: Jun. 16, 2020

(54) ROBOTIC END EFFECTOR WITH ADJUSTABLE INNER DIAMETER

(71) Applicant: Mobius Imaging, LLC, Shirley, MA (US)

(72) Inventor: Russell Stanton, Lunenberg, MA (US)

(73) Assignee: Mobius Imaging, LLC, Shirley, MA (US)

(*) Notice: Subject to any disclaimer, the term of this patent is extended or adjusted under 35 U.S.C. 154(b) by 183 days.

(21) Appl. No.: 15/928,668

(22) Filed: Mar. 22, 2018

(65) Prior Publication Data

US 2018/0271511 A1 Sep. 27, 2018

Related U.S. Application Data

(60) Provisional application No. 62/475,281, filed on Mar. 23, 2017.

(51) Int. Cl.
*A61B 17/02* (2006.01)
*A61B 34/30* (2016.01)
(Continued)

(52) U.S. Cl.
CPC ...... *A61B 17/0218* (2013.01); *A61B 17/3421* (2013.01); *A61B 17/3439* (2013.01); *A61B 34/20* (2016.02); *A61B 6/032* (2013.01); *A61B 6/44* (2013.01); *A61B 17/1604* (2013.01); *A61B 17/32* (2013.01); *A61B 17/8875* (2013.01); *A61B 34/30* (2016.02); *A61B 90/11* (2016.02); *A61B 2017/00367* (2013.01); *A61B 2017/347* (2013.01); *A61B 2034/2055* (2016.02); *A61B 2034/2057* (2016.02); *A61B 2034/2059* (2016.02); *A61B 2034/2065* (2016.02);
(Continued)

(58) Field of Classification Search
CPC .......................... A61B 34/20; A61B 34/2018
See application file for complete search history.

(56) References Cited

U.S. PATENT DOCUMENTS 5,799,055 A  8/1998  Peshkin et al.
5,921,992 A  7/1999  Costales et al.
(Continued)

FOREIGN PATENT DOCUMENTS

CN  201422918 Y  3/2010
CN  201542641 U  8/2010
(Continued)

OTHER PUBLICATIONS

International Search Report for Application No. PCT/US2018/023933 dated Jul. 24, 2018, 4 pages.
(Continued)

*Primary Examiner* — Christian A Sevilla
(74) *Attorney, Agent, or Firm* — Howard & Howard Attorneys PLLC

(57) ABSTRACT

An end effector for a robotic-assisted surgical system having an adjustable inner diameter. In embodiments, the end effector includes a main body having an opening extending through the main body, one or more members located within the main body that extend into and retract from the opening to vary a diameter of the opening through which a tool may be inserted, and an adjustment mechanism on the end effector and coupled to the one or more members for varying the diameter of the opening.

13 Claims, 5 Drawing Sheets

(51) Int. Cl.
  *A61B 34/20* (2016.01)
  *A61B 17/34* (2006.01)
  *A61B 6/03* (2006.01)
  *A61B 90/00* (2016.01)
  *A61B 17/16* (2006.01)
  *A61B 17/88* (2006.01)
  *A61B 17/32* (2006.01)
  *A61B 17/00* (2006.01)
  *A61B 90/11* (2016.01)
  *A61B 6/00* (2006.01)

(52) U.S. Cl.
  CPC ............... *A61B 2090/0807* (2016.02); *A61B 2090/3762* (2016.02); *A61B 2090/3983* (2016.02)

(56) References Cited

U.S. PATENT DOCUMENTS

| | | | |
|---|---|---|---|
| 6,149,592 A | 11/2000 | Yanof et al. | |
| 6,236,875 B1 | 5/2001 | Bucholz et al. | |
| 6,275,725 B1 | 8/2001 | Cosman | |
| 6,533,455 B2 | 3/2003 | Graumann et al. | |
| 6,772,002 B2 | 8/2004 | Schmidt et al. | |
| 6,785,572 B2 | 8/2004 | Yanof et al. | |
| 7,194,120 B2 | 3/2007 | Wicker et al. | |
| 7,251,522 B2 | 7/2007 | Essenreiter et al. | |
| 7,367,973 B2 | 5/2008 | Manzo et al. | |
| 7,587,235 B2 | 9/2009 | Wist et al. | |
| 7,699,877 B2 | 4/2010 | Davison | |
| 7,722,530 B2 | 5/2010 | Davison | |
| 7,799,036 B2 | 9/2010 | Davison et al. | |
| 7,837,612 B2 * | 11/2010 | Gill ..................... | A61B 1/32 600/201 |
| 7,901,380 B2 * | 3/2011 | Ross ................. | A61B 17/3423 604/167.01 |
| 8,016,835 B2 | 9/2011 | Birkmeyer et al. | |
| 8,046,054 B2 | 10/2011 | Kim et al. | |
| 8,118,488 B2 | 2/2012 | Gregerson | |
| 8,126,114 B2 | 2/2012 | Naylor et al. | |
| 8,394,144 B2 | 3/2013 | Zehavi et al. | |
| 8,454,583 B2 | 6/2013 | Perez-Cruet et al. | |
| 8,457,790 B2 | 6/2013 | Blondel et al. | |
| 8,509,503 B2 | 8/2013 | Nahum et al. | |
| 8,761,337 B2 | 6/2014 | Naylor et al. | |
| 8,795,188 B2 | 8/2014 | Maschke | |
| 8,961,406 B2 * | 2/2015 | Ortiz ................. | A61B 17/3423 600/204 |
| 8,974,460 B2 | 3/2015 | De la Fuente Klein et al. | |
| 9,125,680 B2 | 9/2015 | Kostrzewski et al. | |
| 9,237,861 B2 | 1/2016 | Nahum et al. | |
| 9,283,048 B2 | 3/2016 | Kostrzewski et al. | |
| 9,308,050 B2 | 4/2016 | Kostrzewski et al. | |
| 9,545,233 B2 | 1/2017 | Sirpad et al. | |
| 9,550,299 B2 | 1/2017 | Wolf et al. | |
| 9,750,432 B2 | 9/2017 | Nahum et al. | |
| 9,833,292 B2 | 12/2017 | Kostrzewski et al. | |
| 10,004,562 B2 | 6/2018 | Kostrzewski et al. | |
| 10,016,216 B2 * | 7/2018 | Sauter ................ | A61B 17/3462 |
| 10,039,476 B2 | 8/2018 | Nahum et al. | |
| 10,076,385 B2 | 9/2018 | Shoham et al. | |
| 10,136,952 B2 | 11/2018 | Couture et al. | |
| 10,159,534 B2 | 12/2018 | Maillet et al. | |
| 10,405,884 B2 * | 9/2019 | Augelli ............. | A61B 17/3423 |
| 2006/0261303 A1 | 11/2006 | Thomas et al. | |
| 2007/0156157 A1 | 7/2007 | Nahum et al. | |
| 2008/0284114 A1 * | 11/2008 | Price ................. | A61B 17/3423 277/626 |
| 2011/0015650 A1 | 1/2011 | Choi et al. | |
| 2014/0003572 A1 | 1/2014 | Gregerson et al. | |
| 2014/0139215 A1 | 5/2014 | Gregerson et al. | |
| 2014/0249546 A1 | 9/2014 | Shvartsberg et al. | |
| 2014/0265182 A1 | 9/2014 | Stanton et al. | |
| 2014/0275953 A1 | 9/2014 | Gregerson et al. | |
| 2015/0196365 A1 | 7/2015 | Kostrzewski et al. | |
| 2015/0202009 A1 | 7/2015 | Nussbaumer et al. | |
| 2015/0366624 A1 | 12/2015 | Kostrzewski et al. | |
| 2016/0030117 A1 | 2/2016 | Mewes | |
| 2016/0081754 A1 | 3/2016 | Kostrzewski et al. | |
| 2016/0174914 A1 | 6/2016 | Lerch et al. | |
| 2016/0220320 A1 | 8/2016 | Crawford et al. | |
| 2016/0235492 A1 | 8/2016 | Morard et al. | |
| 2016/0278875 A1 | 9/2016 | Crawford et al. | |
| 2017/0071691 A1 | 3/2017 | Crawford et al. | |
| 2017/0079727 A1 | 3/2017 | Crawford et al. | |
| 2017/0165725 A1 * | 6/2017 | Hersey ................... | A61B 90/00 |
| 2017/0172669 A1 | 6/2017 | Berkowitz et al. | |
| 2017/0231702 A1 | 8/2017 | Crawford et al. | |
| 2017/0239002 A1 | 8/2017 | Crawford et al. | |
| 2017/0239003 A1 | 8/2017 | Crawford et al. | |
| 2017/0239006 A1 | 8/2017 | Crawford et al. | |
| 2017/0245951 A1 | 8/2017 | Crawford et al. | |
| 2017/0252112 A1 | 9/2017 | Crawford et al. | |
| 2017/0258533 A1 | 9/2017 | Crawford et al. | |
| 2017/0258535 A1 | 9/2017 | Crawford et al. | |
| 2017/0312039 A1 | 11/2017 | Crawford et al. | |
| 2017/0348061 A1 | 12/2017 | Joshi et al. | |
| 2017/0360513 A1 | 12/2017 | Amiot et al. | |
| 2017/0360517 A1 | 12/2017 | Crawford et al. | |
| 2018/0000546 A1 | 1/2018 | Crawford et al. | |
| 2018/0110573 A1 | 4/2018 | Kostrzewski | |
| 2018/0116739 A1 | 5/2018 | Gogarty et al. | |
| 2018/0116740 A1 | 5/2018 | Gogarty et al. | |
| 2018/0125597 A1 | 5/2018 | Gogarty et al. | |
| 2018/0157238 A1 | 6/2018 | Gogarty et al. | |
| 2018/0221098 A1 | 8/2018 | Forsyth et al. | |
| 2018/0235715 A1 | 8/2018 | Amiot et al. | |
| 2018/0250077 A1 | 9/2018 | Xu et al. | |
| 2018/0256259 A1 | 9/2018 | Crawford | |
| 2018/0271605 A1 | 9/2018 | Kostrzewski et al. | |
| 2018/0346008 A1 | 12/2018 | Nahum et al. | |
| 2019/0000561 A1 | 1/2019 | Decker et al. | |
| 2019/0000569 A1 | 1/2019 | Crawford et al. | |
| 2019/0021795 A1 | 1/2019 | Crawford et al. | |
| 2019/0021799 A1 | 1/2019 | Crawford et al. | |
| 2019/0021800 A1 | 1/2019 | Crawford et al. | |
| 2019/0029759 A1 | 1/2019 | McDonell | |
| 2019/0029765 A1 | 1/2019 | Crawford et al. | |
| 2019/0038362 A1 | 2/2019 | Nash et al. | |
| 2019/0053859 A1 | 2/2019 | Couture et al. | |
| 2019/0069961 A1 | 3/2019 | Smith et al. | |
| 2019/0099222 A1 | 4/2019 | Nahum et al. | |
| 2019/0117313 A1 | 4/2019 | Crawford | |
| 2019/0239964 A1 | 8/2019 | LeBoeuf, II et al. | |
| 2019/0269467 A1 | 9/2019 | Forsyth et al. | |
| 2019/0274765 A1 | 9/2019 | Crawford et al. | |

FOREIGN PATENT DOCUMENTS

| | | |
|---|---|---|
| CN | 101700184 B | 1/2011 |
| CN | 101579269 B | 4/2011 |
| CN | 101853333 B | 11/2012 |
| EP | 2965700 A1 | 1/2016 |
| JP | 2015208824 A | 11/2015 |
| WO | 2015115809 A1 | 8/2015 |
| WO | 2017036340 A1 | 3/2017 |
| WO | 2017122202 A1 | 7/2017 |
| WO | 2018185729 A1 | 10/2018 |

OTHER PUBLICATIONS

English language abstract and machine-assisted English translation for JP 2015-208824 extracted from espacenet.com database on Nov. 6, 2019, 11 pages.

English language abstract and machine-assisted English translation for CN 201422918 extracted from espacenet.com database on Jan. 9, 2020, 7 pages.

English language abstract and machine-assisted English translation for CN 201542641 extracted from espacenet.com database on Jan. 9, 2020, 10 pages.

(56) References Cited

OTHER PUBLICATIONS

English language abstract and machine-assisted English translation for CN 101700184 extracted from espacenet.com database on Jan. 9, 2020, 10 pages.

English language abstract and machine-assisted English translation for CN 101579269 extracted from espacenet.com database on Jan. 9, 2020, 8 pages.

English language abstract and machine-assisted English translation for CN 101853333 extracted from espacenet.com database on Jan. 9, 2020, 9 pages.

English language abstract and machine-assisted English translation for WO 2015/115809 extracted from espacenet.com database on Jan. 9, 2020, 8 pages.

English language abstract for WO 2017/036340 extracted from espacenet.com database on Jan. 9, 2020, 2 pages.

Pal jug, Eric et al. "The JPL Serpentine Robot: a 12 DOF System for Inspection", NASA JPL Technical Reports Server, https://trs.jpl.nasa.gov/handle/2014/29159, Jan. 1, 1995, 5 pages.

\* cited by examiner

ROBOTIC END EFFECTOR WITH ADJUSTABLE INNER DIAMETER

RELATED APPLICATION

This application claims the benefit of priority to U.S. Provisional Application No. 62/475,281, filed Mar. 21, 2017, the entire teachings of which are incorporated herein by reference.

BACKGROUND

Surgical procedures, such as minimally-invasive procedures, may require a surgeon to insert surgical tools inside the body of the patient to a particular depth to reach the target area inside the patient's body. For example, minimally invasive spinal surgical procedures have been used for stabilization of vertebral bones and spinal joints and for relieving of pressure applied to the spinal nerves. Such procedures may utilize relatively small incisions and insertion of tubular retractors and cannulas while minimizing damage to muscles and other surrounding anatomical features. Minimally invasive surgical approaches can be faster, safer and require less recovery time than conventional open surgeries. There is a continuing need for improvement to the safety and speed of surgical procedures, such as minimally-invasive surgical procedures.

SUMMARY

Various embodiments include an end effector for a robotic-assisted surgical system that has an adjustable inner diameter. In embodiments, an end effector includes a main body having an opening extending through the main body, one or more members located within the main body that extend into and retract from the opening to vary a diameter of the opening through which a tool may be inserted, and an adjustment mechanism on the end effector and coupled to the one or more members for varying the diameter of the opening.

Further embodiment include a method of inserting a tool into the body of a patient that includes positioning an end effector over the body of the patient such that an opening extending through the end effector defines a trajectory into the body of the patient, using an adjustment mechanism to vary a size of a working channel through the opening of the end effector such that the diameter of the working channel corresponds with an outer diameter of the tool, and inserting the tool through the working channel of the end effector along the defined trajectory and into the body of the patient.

BRIEF DESCRIPTION OF THE DRAWINGS

Other features and advantages of the present invention will be apparent from the following detailed description of the invention, taken in conjunction with the accompanying drawings of which.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Various embodiments include an end effector for a robotic arm that includes a hollow tube or cannula through which one or more tools, such as an invasive surgical tool, may be inserted. The end effector according to various embodiments may have an adjustable inner diameter to enable tools of different sizes to be accurately guided through the interior of the end effector.

Figure 1:
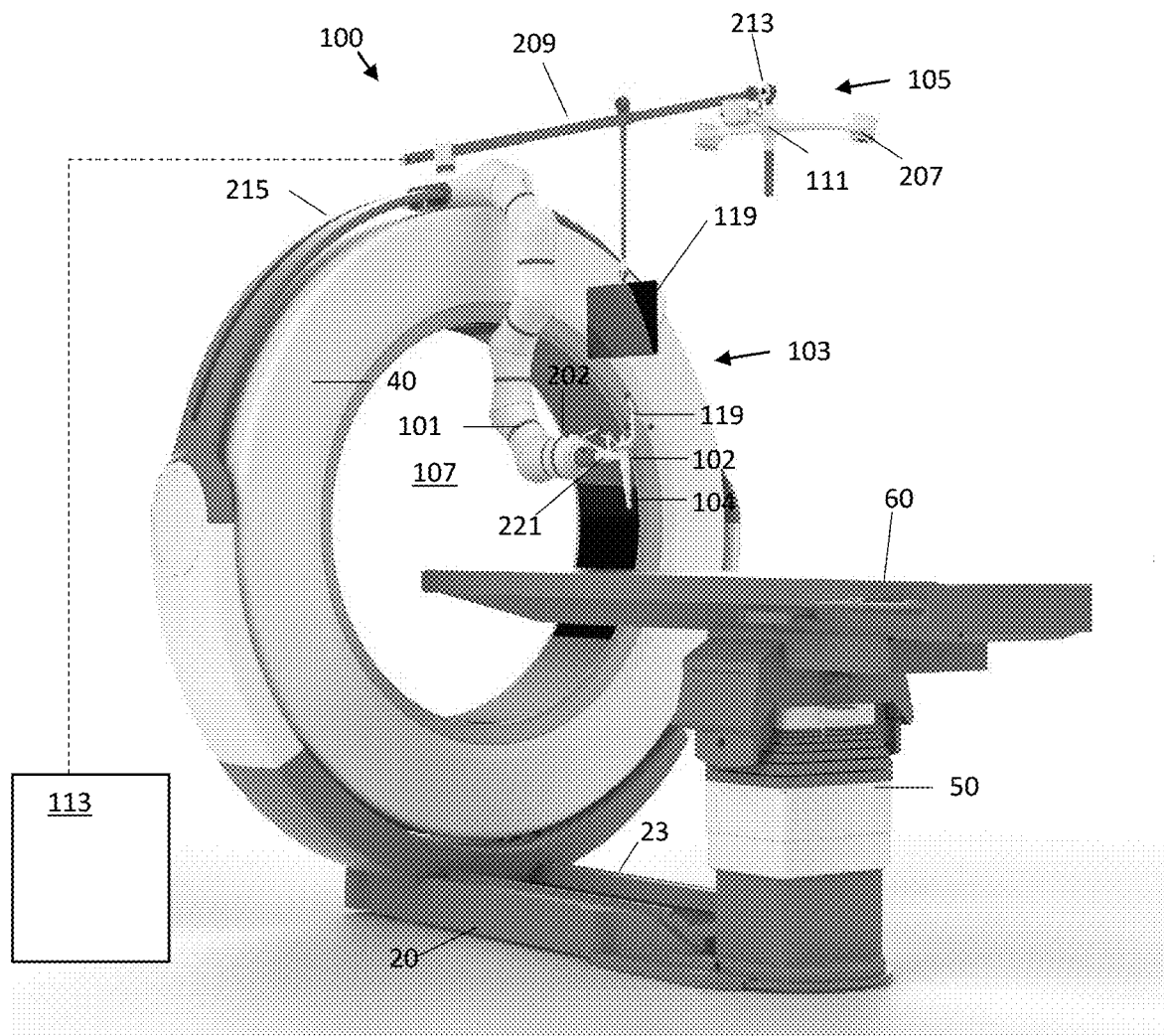
FIG. 1 illustrates a robotic-assisted surgical system for use with an adjustable diameter end effector according to an embodiment.

FIG. 1 illustrates a system 100 for performing computer-assisted image-guided surgery that may utilize an end effector 102 having an adjustable inner diameter according to various embodiments. The system 100 in this embodiment includes an imaging device 103, a motion tracking system 105 and a robotic arm 101 for performing a robotically-assisted surgical procedure. The robotic arm 101 may be fixed to a support structure at one end and may have an adjustable-diameter end effector 102 located at the other end of the robotic arm 101. The robotic arm 101 may comprise a multi joint arm that includes a plurality of linkages connected by joints having actuator(s) and optional encoder(s) to enable the linkages to rotate, bend and/or translate relative to one another in response to control signals from a robot control system. The motions of the robotic arm 101 may enable the end effector 102 to be moved to various positions and/or orientations, such as various positions and/or orientations with respect to a patient (not illustrated) that may be located on a patient support 60 (e.g., surgical table).

The imaging device 103 may be used to obtain diagnostic images of a patient (not shown in FIG. 1), which may be a human or animal patient. In embodiments, the imaging device 103 may be an x-ray computed tomography (CT) imaging device. The patient may be positioned within a central bore 107 of the imaging device 103 and an x-ray source and detector may be rotated around the bore 107 to obtain x-ray image data (e.g., raw x-ray projection data) of the patient. The collected image data may be processed using a suitable processor (e.g., computer) to perform a three-dimensional reconstruction of the object. In other embodiments, the imaging device 103 may comprise one or more of an x-ray fluoroscopic imaging device, a magnetic resonance (MR) imaging device, a positron emission tomography (PET) imaging device, a single-photon emission computed tomography (SPECT), or an ultrasound imaging device. In embodiments, image data may be obtained pre-operatively (i.e., prior to performing a surgical procedure), intra-operatively (i.e., during a surgical procedure) or post-operatively (i.e., following a surgical procedure) by positioning the patient within the bore 107 of the imaging device 103. In the system 100 of FIG. 1, this may be accomplished by moving the imaging device 103 over the patient to perform a scan while the patient may remain stationary.

Examples of x-ray CT imaging devices that may be used according to various embodiments are described in, for example, U.S. Pat. No. 8,118,488, U.S. Patent Application Publication No. 2014/0139215, U.S. Patent Application Publication No. 2014/0003572, U.S. Patent Application Publication No. 2014/0265182 and U.S. Patent Application Publication No. 2014/0275953, the entire contents of all of which are incorporated herein by reference. In the embodiment shown in FIG. 1, the patient support 60 (e.g., surgical table) upon which the patient may be located is secured to the imaging device 103, such as via a column 50 which is mounted to a base 20 of the imaging device 103. A portion of the imaging device 103 (e.g., an O-shaped imaging gantry 40) which includes at least one imaging component may translate along the length of the base 20 on rails 23 to perform an imaging scan of the patient, and may translate away from the patient to an out-of-the-way position for performing a surgical procedure on the patient. It will be understood that other imaging devices may be utilized, including other mobile or fixed x-ray CT devices or a C-arm x-ray fluoroscopy device.

Further, although the imaging device 103 shown in FIG. 1 is located close to the patient within the surgical theater, the imaging device 103 may be located remote from the surgical theater, such as in another room or building (e.g., in a hospital radiology department).

The motion tracking system 105 shown in FIG. 1 includes a plurality of marker devices 119, 202 and an optical sensor device 111. Various systems and technologies exist for tracking the position (including location and/or orientation) of objects as they move within a three-dimensional space. Such systems may include a plurality of active or passive markers fixed to the object(s) to be tracked and a sensing device that detects radiation emitted by or reflected from the markers. A 3D model of the space may be constructed in software based on the signals detected by the sensing device.

The motion tracking system 105 in the embodiment of FIG. 1 includes a plurality of marker devices 119, 202 and a stereoscopic optical sensor device 111 that includes two or more cameras 207 (e.g., IR cameras). The optical sensor device 111 may include one or more radiation sources (e.g., diode ring(s)) that direct radiation (e.g., IR radiation) into the surgical field, where the radiation may be reflected by the marker devices 119, 202 and received by the cameras. The marker devices 119, 202 may each include three or more (e.g., four) reflecting spheres, which the motion tracking system 105 may use to construct a coordinate system for each of the marker devices 119, 202. A computer 113 may be coupled to the sensor device 111 and may determine the transformations between each of the marker devices 119, 202 and the cameras using, for example, triangulation techniques. A 3D model of the surgical space in a common coordinate system may be generated and continually updated using motion tracking software implemented by the computer 113. In embodiments, the computer 113 may also receive image data from the imaging device 103 and may register the image data to the common coordinate system as the motion tracking system 105 using image registration techniques as are known in the art. In embodiments, at least one reference marker device 115 may be attached to the patient 200, as shown in FIGS. 2A-2C. The reference marker device 115 may be rigidly attached to a landmark in the anatomical region of interest (e.g., clamped or otherwise attached to a bony portion of the patient's anatomy) to enable the anatomical region of interest to be continually tracked by the motion tracking system 105. Additional marker devices 119 may be attached to surgical tools or instruments 104 to enable the tools/instruments 104 to be tracked within the common coordinate system. Another marker device 202 may be rigidly attached to the robotic arm 101, such as on the end effector 102 of the robotic arm 101, to enable the position of robotic arm 101 and end effector 102 to be tracked using the motion tracking system 105. The computer 113 may also include software configured to perform a transform between the joint coordinates of the robotic arm 101 and the common coordinate system of the motion tracking system 105, which may enable the position and orientation of the end effector 102 of the robotic arm 101 to be controlled with respect to the patient 200.

In addition to passive marker devices described above, the motion tracking system 105 may alternately utilize active marker devices that may include radiation emitters (e.g., LEDs) that may emit radiation that is detected by an optical sensor device 111. Each active marker device or sets of active marker devices attached to a particular object may emit radiation in a pre-determined strobe pattern (e.g., with modulated pulse width, pulse rate, time slot and/or amplitude) and/or wavelength which may enable different objects to be uniquely identified and tracked by the motion tracking system 105. One or more active marker devices may be fixed relative to the patient, such as secured to the patient's skin via an adhesive membrane or mask. Additional active marker devices may be fixed to surgical tools 104 and/or to the end effector 102 of the robotic arm 101 to allow these objects to be tracked relative to the patient.

In further embodiments, the marker devices may be passive maker devices that include moiré patterns that may enable their position and orientation to be tracked in three-dimensional space using a single camera using Moiré Phase Tracking (MPT) technology. Other tracking technologies, such as computer vision systems and/or magnetic-based tracking systems, may also be utilized.

As shown in FIG. 1, the optical sensor device 111 may include a plurality of cameras 207 mounted to an arm 209 extending above the patient surgical area. The arm 209 may be mounted to or above the imaging device 103. The arm 209 may enable the sensor device 111 to pivot with respect to the arm 209 and/or the imaging device 103 (e.g., via one or more ball joints 213). The arm 209 may enable a user to adjust the position and/or orientation of the sensor device 111 to provide the cameras 207 with a clear view into the surgical field while avoiding obstructions. The arm 209 may enable the position and/or orientation of the sensor device 111 to be adjusted and then locked in place during an imaging scan or surgical procedure.

The system 100 may also include at least one display device 119 as illustrated in FIG. 1. The display device 119 may display image data of the patient's anatomy obtained by the imaging device 103. In the case of CT image data, for example, the display device 119 may display a three-dimensional volume rendering of a portion of the patient's anatomy and/or may display two-dimensional slices (e.g., axial, sagittal and/or coronal slices) through the 3D CT reconstruction dataset. The display device 119 may facilitate planning for a surgical procedure, such as by enabling a surgeon to define one or more target positions in the patient's body and/or a path or trajectory into the patient's body for inserting surgical tool(s) to reach a target position while minimizing damage to other tissue or organs of the patient. The position and/or orientation of one or more objects tracked by the motion tracking system 105 may be shown on the display 119, and may be shown overlaying the image data. The use of tracked surgical instruments or tools in combination with pre-operative or intra-operative images of the patient's anatomy in order to guide a surgical procedure may be referred to as "image-guided surgery."

In embodiments, the display device 119 may be a handheld computing device, such as a tablet device. One or more handheld display devices 119 may be mounted to an arm 209 extending above the patient surgical area, as shown in FIG. 1. The arm 209 may also support the optical sensing device 111 for the motion tracking system 105, as described above. In other embodiments, a handheld display device 119 may be mounted to the patient support 60 or column 50 or to any portion of the imaging system 103, or to any of the wall, ceiling or floor in the operating room, or to a separate cart. Alternately or in addition, the at least one display device 119 may be a monitor display that may be located on a mobile cart or mounted to another structure (e.g., a wall) within the surgical theater. In further embodiments, a display device 119 may be a head-mounted display that may be worn by a surgeon or other clinician.

As shown in FIG. 1, the robotic arm 101 may be fixed to the imaging device 103, such as on a support element 215 (e.g., a curved rail) that may extend concentrically over the outer surface of the O-shaped gantry 40 of the imaging device 103. In embodiments, an arm 209 to which the optical sensing device 111 is mounted may be mounted to the same or a similar support element 215 (e.g., curved rail) as the robotic arm 101. The position of the robotic arm 101 and/or the arm 209 may be adjustable along the length of the support element 215. In other embodiments, the robotic arm 101 may be secured to any other portion of the imaging device 103, such as directly mounted to the gantry 40. Alternatively, the robotic arm 101 may be mounted to the patient support 60 or column 50, to any of the wall, ceiling or floor in the operating room, or to a separate cart. Although a single robotic arm 101 is shown in FIG. 1, it will be understood that two or more robotic arms 101 may be utilized. Each robotic arm 101 may include an end effector 102 with an adjustable internal diameter opening, as described in further detail below.

The at least one robotic arm 101 may aid in the performance of a surgical procedure, such as a minimally-invasive spinal surgical procedure or various other types of orthopedic, neurological, cardiothoracic and general surgical procedures. In embodiments, the motion tracking system 105 may track the position of the robotic arm 101 (e.g., via marker device 202 on end effector 102 as shown in FIG. 1) within the patient coordinate system. A control loop may continuously read the tracking data and the current parameters (e.g., joint parameters) of the robotic arm 101 and may send instructions to a robotic controller to cause the robotic arm 101 to move to a desired position and orientation within the patient coordinate system.

In embodiments, a surgeon may use an image-guided surgery system as a planning tool for a surgical procedure, such as by setting trajectories within the patient for inserting surgical tools, as well as by selecting one or more target locations for a surgical intervention within the patient's body. The trajectories and/or target locations set by the surgeon may be saved (e.g., in a memory of a computer device, such as computer device 113 shown in FIG. 1) for later use during surgery. In embodiments, the surgeon may be able to select stored trajectories and/or target locations using an image guided surgery system, and the robotic arm 101 may be controlled to perform a particular movement based on the selected trajectory and/or target location. For example, the robotic arm 101 may be moved to position the end effector 102 of the robotic arm 101 into alignment with the pre-defined trajectory and/or over the pre-determined target location. The hollow tube or cannula extending through the end effector 102 may be used to guide an instrument 104 into the patient's body along the pre-defined trajectory and/or to the pre-defined target location.

In addition to a robotic arm 101 as described above, an end effector 102 of the present embodiments may be attached to a moveable arm or boom, which may be motor-driven or manually moved. The arm may be moved to position the end effector 102 at a desired location with respect to the patient and the arm may be configured to hold its pose during a surgical intervention.

Figure 2:
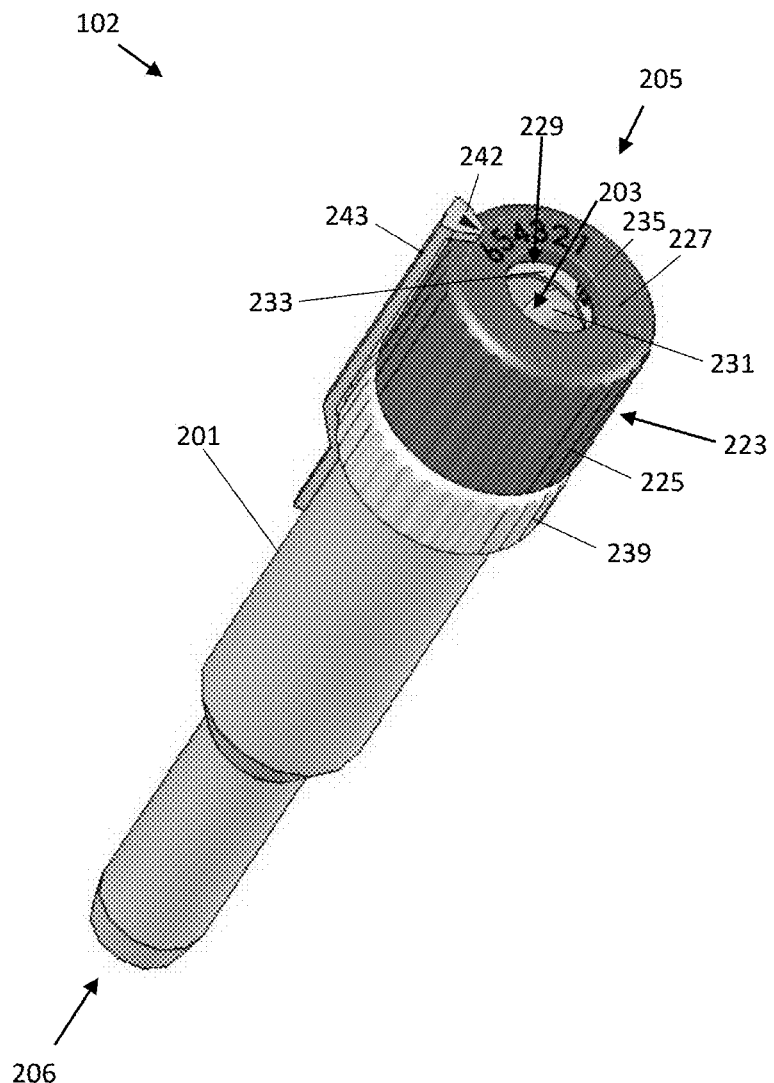
FIG. 2 is a perspective view of an end effector according to an embodiment.
Figure 3:
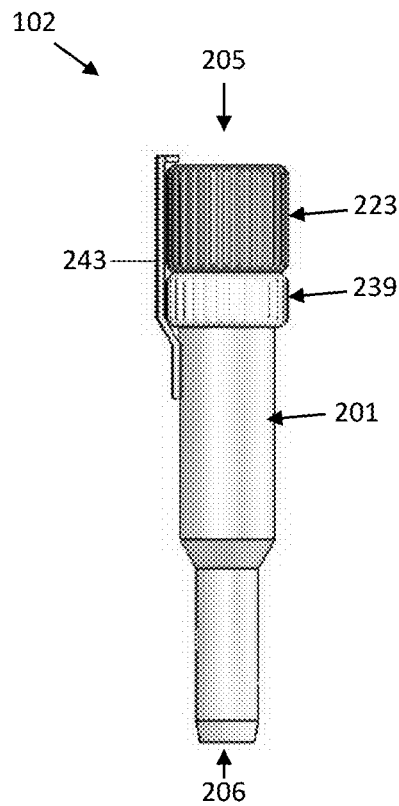
FIG. 3 is a side elevation view of the end effector shown in FIG. 2.
Figure 4:
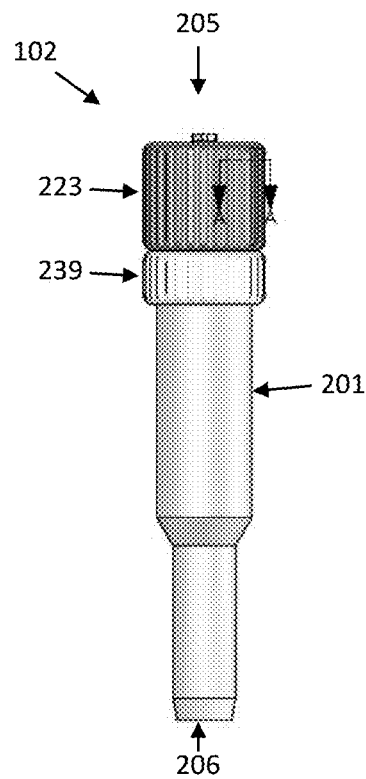
FIG. 4 is a rear elevation view of the end effector shown in FIG. 2.

An embodiment of an end effector 102 having an adjustable-diameter internal cannula is illustrated in FIGS. 2-6C. The end effector 102 may be utilized in a system 100 such as shown in FIG. 1. The end effector 102 in this embodiment includes an elongated main body 201 having a central opening 203 extending through the main body 201. The main body 201 may have a generally cylindrical outer shape. In some embodiments, such as shown in FIGS. 2-4, the main body 201 may have a stepped or tapered outer width (e.g., diameter) along its length, and may be wider at a first end 205 than at a second end 206. Alternately, the outer width of the main body 201 may be substantially constant along its length.

A connecting member 221 (see FIG. 1) may extend from a side of the main body 201 and may be used to secure the end effector 102 to the end of a robotic arm 101. In embodiments, the main body 201 and the connecting member 221 may be permanently connected (e.g., integrally-formed components and/or connected by an adhesive or mechanical fasteners). In other embodiments, the main body 201 and the connecting member 221 may be separate components that may be joined to form an end effector 102 as shown in FIG. 1. For example, the connecting member 221 may have an opening (e.g., a cylindrical-shaped opening) extending through the connector that is sized and shaped to receive the main body 201 within the opening. Alternately or in addition, the connecting member 221 and the main body 201 may have mating features that enable the main body 201 to snap onto or otherwise attach to the connecting member 221. In some embodiments, the connecting member 221 may not be utilized, and the main body 201 of the end effector 102 may directly attach to the robotic arm 101.

The end effector 102 may be a sterile or sterilizable component that may not need to be draped during surgery. In some embodiments, the end effector 102 may be attached to a robotic arm 101 over a surgical drape that covers the arm 101. The end effector 102 may be a single-use disposable component, or a multi-use component that may be re-sterilized (e.g., autoclavable). The end effector 102 may have a marker device 202 (e.g., an array of reflective spheres mounted to a rigid frame) attached to the end effector 102 to enable the end effector 102 to be tracked by a motion tracking system 105, such as shown in FIG. 1.

Referring again to FIGS. 2-4, a collar 223 may be located proximate to the first end 205 of the main body 201. The collar 223 may include a first portion 225 that extends over a portion of the outer surface of the main body 201 and an end portion 227 that is located over the first end 205 of the main body 201. The end portion 227 may include an opening 229 that is aligned with the central opening 203 extending through the main body 201 of the end effector 102. The first portion 225 of the collar 223 may also include a ridged/fluted outer surface to enable the collar 223 to be easily gripped and manipulated.

The collar 223 may be rotatable with respect to the main body 201 of the end effector 102. The rotation of the collar 223 on the main body 201 may cause a variation in the internal diameter of the central opening 203. For example, the rotation of the collar 223 may drive the extension and retraction of one or more members (e.g., flutes 231) towards or away from the interior side wall of the main body 201 to increase or decrease a size of a void space within the main body 201 through which a surgical instrument or other tool may pass.

Figure 5:
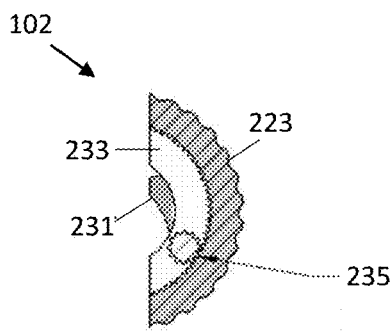
FIG. 5 is a partial cross-section view of an embodiment end effector viewed along line A-A in FIG. 4.
Figure 6A:
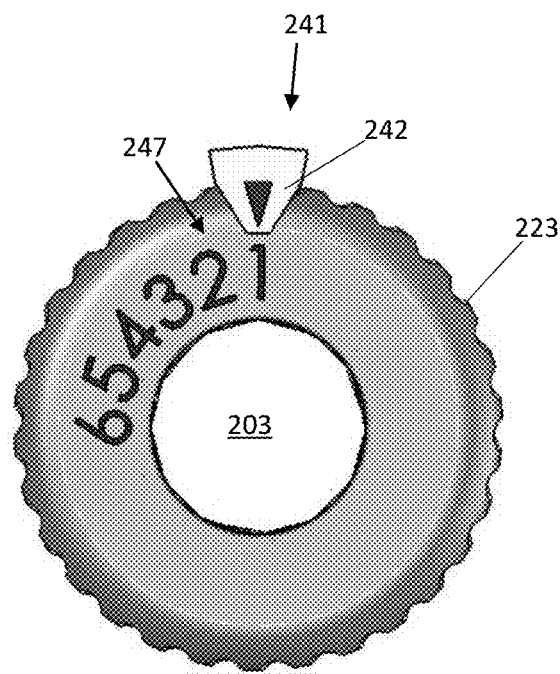
FIGS. 6A-6C are top views of an end effector illustrating a plurality of moveable flutes in different configurations to provide a central opening having a varying diameter.
Figure 6B:
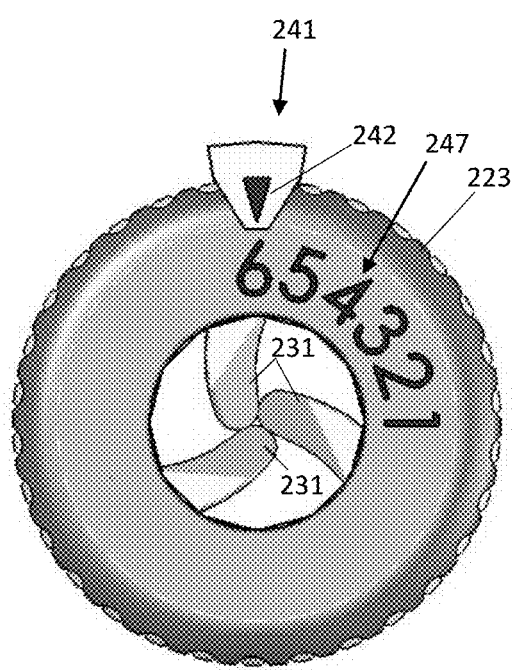
Figure 6C:
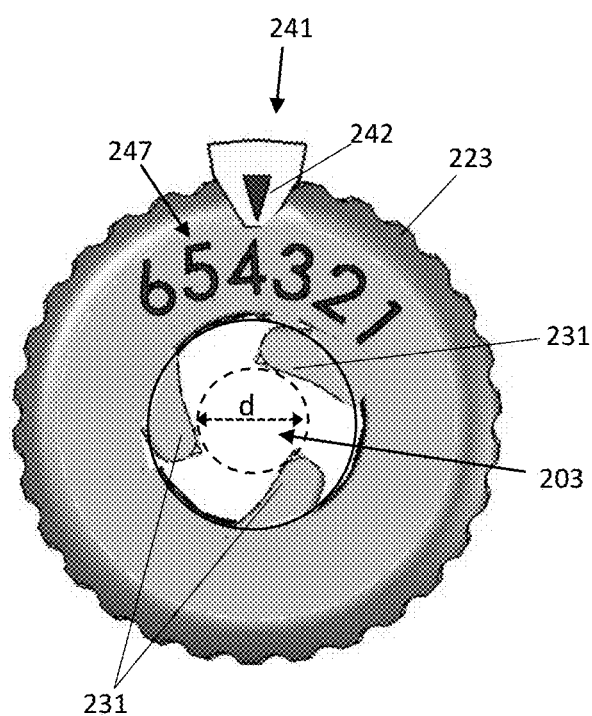

An example of a mechanism for adjusting the internal diameter of an end effector 102 is shown in FIGS. 5-6C. FIG. 5 is a partial cross-section view of the end effector 102 taken along line A-A in FIG. 4. As shown in FIG. 5, the main body 201 of the end effector 102 includes a flange 233 extending from the interior sidewall of the main body 201. A gear 235 is located on a first side of the flange 233 and is coupled to a flute 231 located on the opposite side of the flange 233. The rotation of the gear 235 causes the flute 231 to pivot towards and away from the interior sidewall of the main body 201. The teeth of the gear 235 engage with corresponding teeth extending on an interior surface 237 of the collar 223. Thus, as the collar 223 is turned, the flute 231 is pivoted outwards and inwards with respect to the interior sidewall of the main body 201.

The end effector 102 may have a plurality of flutes 231 coupled to corresponding gears 235 that may similarly pivot out and back with respect to the main body 201 as the collar 223 is turned to adjust the internal diameter of the central opening 203. For example, three flutes 231 may be equally spaced around the periphery of the main body 201. The flutes 231 may be pivotable between a first configuration shown in FIG. 6A, in which the flutes 231 are positioned against the sidewall of the main body 201 to provide a maximum amount of clearance through the central opening 203, and a second configuration shown in FIG. 6B in which the flutes 231 are pivoted out to their maximum extent such that their tip ends contact one another and the clearance through the center of the central opening 203 is at its minimal extent. The flutes 231 may also be moved to an intermediate configuration between the configurations of FIGS. 6A and 6B. For example, FIG. 6C illustrates the flutes 231 pivoted out such that the tip ends of the flutes 231 define a central opening 203 (i.e., a working channel) having a diameter, d. A tool having a cross-sectional dimension (e.g., diameter) that is approximately equal to diameter d may be inserted through the central opening 203. The tool may slide past the flutes 231 along the length of the main body 201 and out through the second end 206 of the main body 201 (e.g., into the body of a patient). The flutes 231 may guide the advancement of the tool along a fixed trajectory (e.g., along the central axis of the main body 201) and may prevent radial motion of the tool within the main body 201. In some embodiments, the flutes 231 may be further tightened against a tool located within the main body 201 by rotating the collar 223 so as to fix the longitudinal position of the tool within the main body 201.

Although the embodiment shown in FIGS. 6A-6C includes three flutes 231, it will be understood that other embodiments may include a different number (e.g., 4, 5, 6, etc.) of flutes 231 that may extend and retract within the main body 201 to adjust the interior diameter of the opening 203 through which a tool/instrument may be inserted. The plurality of flutes 231 may be moveable within the main body 201 using a suitable mechanism, and may be self-centering, as in the embodiment shown in FIGS. 5-6C.

The end effector 102 may also include a locking mechanism that may be engaged to hold the position of the flutes 231 within the main body 201. In the embodiment shown in FIGS. 2-4, the locking mechanism may be a second collar 239 (a locking collar) located on the main body 201 adjacent to collar 223. The second collar 239 may be engaged to prevent collar 223 from rotating on the main body 201 and may be disengaged to allow the collar 223 to rotate on the main body 201.

In embodiments, the second collar 239 may be engaged to lock the rotation of collar 223 by moving the second collar 239 into contact with collar 223. The second collar 239 may be disengaged by moving the second collar 239 out of contact with collar 223. In one embodiment, the second collar 239 may be moved into contact with collar 223 to provide an interference fit between the two collars 223, 239 that prevents collar 223 from rotating on the main body 201. Alternately or in addition, the two collars 223, 239 may include mating features that engage with one another to prevent collar 223 from rotating. In embodiments, the second collar 239 may be threaded onto the outer surface of the main body 201, and may be tightened against the collar 223 to prevent the collar 223 from rotating, and may be backed away from the collar 223 to allow the collar 223 to rotate. In an alternative embodiment, the second collar 239 may be spring-biased against collar 223 to prevent the collar 223 from rotating, and may be pushed away from the collar 223 to allow the collar 223 to rotate. It will be understood that other mechanisms for locking and unlocking the collar 223 may also be utilized.

The adjustable-diameter end effector 102 may also include an indicator, such as a dial indicator 241, that provides an indication of the internal diameter of the central opening 203 through which a tool may be inserted. As shown in FIGS. 2 and 6A-6C, the dial indicator 241 may include a reference indicator 242 that may be fixed to the main body 201, such as via a cantilevered arm 243 that extends from the side of the main body 201 over the end portion 227 of the collar 223. Graduated markings 247 may be located on the end portion 223 of the collar 223. The markings 247 may be calibrated to indicate the internal diameter of the opening 203 as the collar 223 is turned on the main body 201. Rotating the collar 223 in a first direction (e.g., counter-clockwise) may increase the diameter of the opening 203 and rotating the collar 223 in a second dimension (e.g., clockwise) may decrease the diameter of the opening 203.

In various embodiments, the end effector 102 may be easily adjusted to accommodate various-sized surgical instruments/tools that may be inserted through the end effector 102 while maintaining a desired trajectory into a patient. Examples of such tools/instruments include, without limitation, a needle, a cannula, an awl, a drill, a screw driver, a screw, and implant, a tool for gripping or cutting, an electrode, a radiation source, and an endoscope.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

What is claimed is:

1. An end effector for a surgical robotic system, comprising:
    a main body having an opening extending through the main body;
    one or more members located within the main body that extend into and retract from the opening to vary a diameter of the opening through which a tool may be inserted, the one or more members comprising a plurality of flutes that are pivotable towards and away from an interior sidewall of the main body to vary the diameter of the opening; and
    an adjustment mechanism on the end effector and coupled to the one or more members for varying the diameter of the opening, the adjustment mechanism comprising a collar located over the main body and coupled to the plurality of flutes such that rotation of the collar in a first direction relative to the main body causes the plurality of flutes to pivot away from the interior sidewall of the main body to reduce the diameter of the opening, and rotation of the collar in a second direction relative to the main body causes the plurality of flutes to pivot towards the interior sidewall of the main body to increase the diameter of the opening.

2. The end effector of claim 1, wherein each of the flutes is coupled to a gear that engages with an interior surface of the collar such that a rotation of the collar on the main body causes the flute to pivot with respect to the main body.

3. The end effector of claim 1, wherein the plurality of flutes are self-centering.

4. The end effector of claim 1, further comprising:
    a locking mechanism that is engageable to hold the positions of the plurality of flutes within the main body.

5. The end effector of claim 4, wherein the collar is a first collar and the locking mechanism comprises a second collar located over the main body.

6. The end effector of claim 5, wherein the second collar is moveable on the main body between a first position, in which the second collar contacts against the first collar to prevent the first collar from rotating relative to the main body, and a second position, in which the second collar is moved away from the first collar to enable the first collar to rotate with respect to the main body.

7. The end effector of claim 1, further comprising a dial indicator that provides an indication of the diameter of the opening.

8. The end effector of claim 7, wherein the dial indicator includes a reference indicator fixed to the main body and graduated markings located on the collar.

9. The end effector of claim 1, further comprising a connecting member that extends from a side surface of the main body and attaches to a robotic arm.

10. The end effector of claim 1, further comprising a marker device fixed to the end effector that enables the end effector to be tracked using a motion tracking system.

11. A method of inserting a tool into the body of a patient, comprising:
    positioning a main body of an end effector over the body of the patient such that an opening extending through the main body defines a trajectory into the body of the patient;
    using an adjustment mechanism comprising a collar located over the main body and coupled to a plurality of flutes located within the main body to vary a size of a working channel through the opening of the end effector by rotating the collar relative to the main body to pivot the plurality of flutes relative to an interior sidewall of the main body to vary the size of the working channel such that the diameter of the working channel corresponds with an outer diameter of the tool; and
    inserting the tool through the working channel of the end effector along the defined trajectory and into the body of the patient.

12. The method of claim 11, wherein the tool comprises at least one of a needle, a cannula, an awl, a drill, a screw driver, a screw, and implant, a tool for gripping or cutting, an electrode, a radiation source, and an endoscope.

13. The method of claim 11, wherein positioning the end effector comprises controlling a robotic arm to move the end effector to a position such that the opening extending through the main body is aligned with a pre-defined trajectory into the body of the patient.

* * * * *